United States Patent [19]
Czar et al.

[11] Patent Number: 5,284,146
[45] Date of Patent: Feb. 8, 1994

[54] REMOVABLE IMPLANTED DEVICE

[75] Inventors: Carl T. Czar, Shoreview; Edward J. Mikolajczyk, Minneapolis, both of Minn.

[73] Assignee: Applied Biometrics Inc., Eden Prairie, Minn.

[21] Appl. No.: 23,193

[22] Filed: Feb. 25, 1993

Related U.S. Application Data

[62] Division of Ser. No. 709,343, Jun. 3, 1991, Pat. No. 5,205,292.

[51] Int. Cl.⁵ .............................................. A61B 8/12
[52] U.S. Cl. .............................. 128/662.03; 604/175; 607/132
[58] Field of Search ............. 128/661.08–661.1, 128/662.01, 662.03–662.06, 691, 692; 604/175; 607/132; 606/138, 148

[56] References Cited

U.S. PATENT DOCUMENTS

| | | | |
|---|---|---|---|
| 4,674,336 | 6/1987 | Johnston | 128/662.04 |
| 4,722,347 | 2/1988 | Abrams et al. | 128/662.04 |
| 4,733,669 | 3/1988 | Segal | 128/662.04 |
| 4,886,059 | 12/1989 | Weber | 128/207.15 |
| 5,121,749 | 6/1992 | Nassi et al. | 128/692 |
| 5,205,292 | 4/1993 | Czar et al. | 128/662.03 |

Primary Examiner—Angela D. Sykes
Attorney, Agent, or Firm—Vidas, Arrett & Steinkraus

[57] ABSTRACT

An implantable, extractable probe for attachment to a vessel or organ. The probe is made up of an elongate probe body having front and rear ends, and top and bottom sides, the elongate probe body terminating in a flexible tube. The probe has at least one biological sensor attached to the bottom side of the probe body with at least one lead wire connected to the biological sensor, and the lead wire extends through the flexible tube. The probe includes a suture attachment wire for attaching at least one suture to secure the probe body to a predetermined sensor site, the suture attachment wire being releasably connected to the front of the elongate probe body and extending through the flexible tube, at least a portion of the suture attachment wire extending between the front of the elongate probe body and the flexible tube such that it is spaced a predetermined distance from the probe body. The probe may be secured to a predetermined sensor site by attaching at least one suture to the suture attachment wire, such that when the suture attachment wire is released, the probe body is released for extraction from the body.

3 Claims, 2 Drawing Sheets

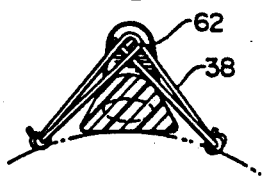
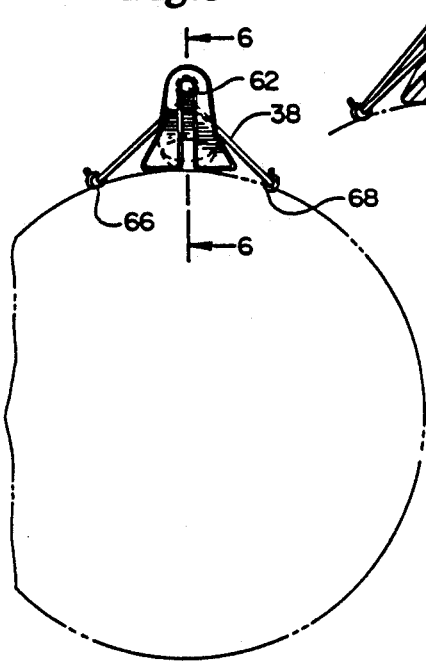
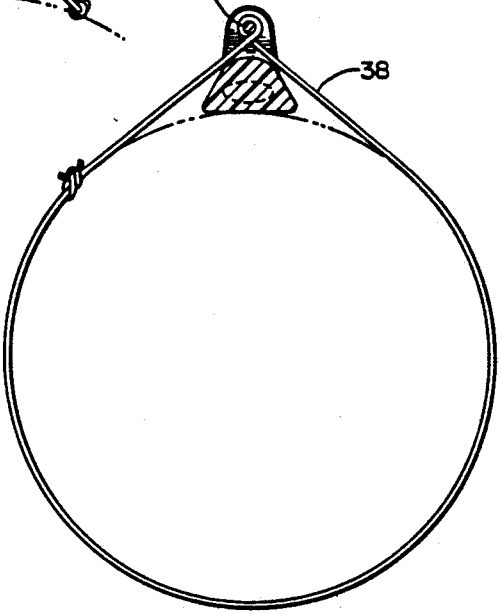
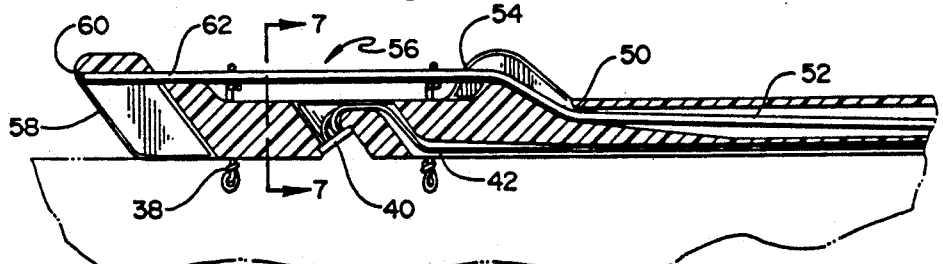
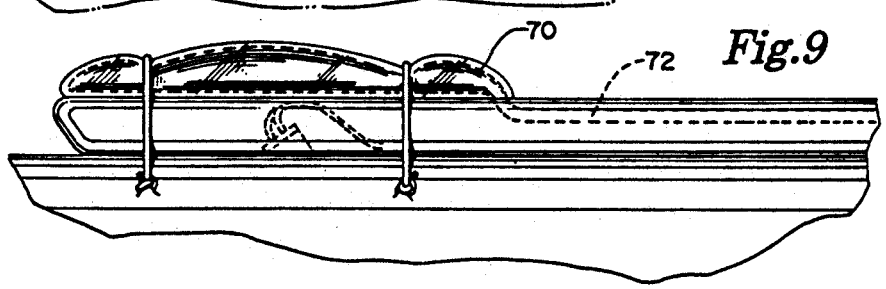
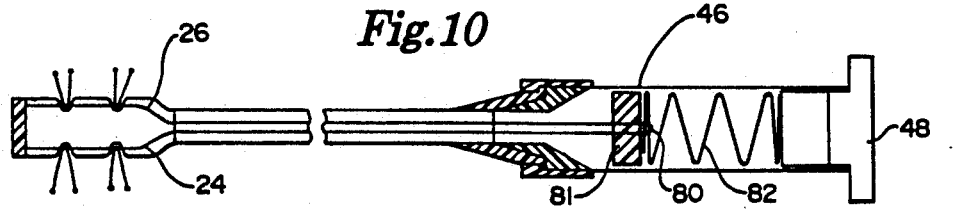

REMOVABLE IMPLANTED DEVICE

This is a divisional of copending application Ser. No. 07/709,343 filed on Jun. 3, 1991 now U.S. Pat. No. 5,205,292.

BACKGROUND OF THE INVENTION

1. Field Of The Invention

This invention relates to a removable implanted device, and more particularly, to a ultrasound sensor for measuring blood flow which can be implanted, then removed from the patient without reopening the implant wound.

2. Description Of The Related Art

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

U.S. Pat. No. 3,661,146, entitled "Transducer Arrangement For Measuring Blood Flow", issued May 9, 1972 to Peronneau, is directed to a transducer for measuring the speed and flow of blood. The transducer is fixed to the vessel with a band of dacron which is sutured shut. This device does not allow for removal without reopening the wound.

U.S. Pat. No. 4,313,448, entitled "Myocardial Sutureless Lead", issued Feb. 2, 1982 to Stokes, is directed to a device which anchors itself in tissue using a barbed end. This device does not utilize sutures in conjunction with a wire to allow for removal without reopening the wound.

U.S. Pat. No. 4,355,643, entitled "Vacuum Cup Doppler Flow Transducer And Method For Using Same", issued Oct. 26, 1982 to Laughlin, is directed to a device which uses a suction cup to create a vacuum, and thereby attach the device to the vessel.

U.S. Pat. No. 4,541,433, entitled "Cardiac Output Monitor", issued Sep. 17, 1985 to Baudino, is directed to a device which uses a pair of fixation wires, which puncture the vessel and secure the instrument to the vessel.

U.S. Pat. No. 4,671,295, entitled "Method For Measuring Cardiac Output", issued Jun. 9, 1987 to Abrams, is directed to a device which does not require surgery. This device is inserted through the nasal or oral cavity.

U.S. Pat. No. 4,722,347, entitled "Apparatus For Measuring Cardiac Output", issued Feb. 2, 1988 to Abrams, is similar to U.S. Pat. No. 4,671,295.

U.S. Pat. No. 4,823,800, entitled "Implantable Ultrasonic Probe And Method Of Manufacturing The Same", issued Apr. 25, 1989 to Compos, is directed to a device which may be removed without a complex procedure.

U.S. Pat. No. 4,915,113, entitled "Method And Apparatus For Monitoring The Patency Of Vascular Grafts", issued Apr. 10, 1990 to Holman, is directed to an implantable device which is anchored to the vessel using a collar (see FIG. 2). This reference is not considered anticipatory or suggestive of the proposed invention.

U.S. Pat. No. 4,917,115, entitled "Pacing System And Method For Physiological Stimulation Of The Heart Utilizing Doppler Means", issued Apr. 17, 1990 to Flammang, is directed to a cardiac pacing device.

U.S. Pat. No. 4,926,875, entitled "Implantable And Extractable Biological Sensor Probe", issued May 22, 1990 to Rabinovitz, is directed to a probe body 10 which includes a doppler transducer to sense blood flow, and which is wrapped around the vessel and secured using suture 34 and release wire 28 (see FIG. 1, 1b). To release the device wire 28 is pulled back, releasing suture 34 and allowing the probe 10 to unwarp. The device is then gently pulled out of the patient without surgery.

U.S. Pat. No. 4,947,854, entitled "Epicardial Multifunctional Probe", issued Aug. 14, 1990 to Rabinovitz, is directed to a implanted device which measures blood flow velocity and muscle thickening with two sensors.

SUMMARY OF THE INVENTION

Prior art implantable, extractable sensors are cumbersome to use and place undue stress on the vessel or organ during removal. Applicant's inventive device allows for easy placement on the monitoring site, most commonly a vessel, and allows for ease of removal without unduly stressing the vessel or organ.

Applicant's device is comprised of a probe body attached to a flexible tube. The probe body houses a doppler sensor for monitoring blood flow, typically through a vessel. A suture attachment wire extends through the flexible tube and terminates at the distal end of the probe body. A portion of the attachment wire is exposed and spaced a distance from the probe body so as to allow sutures to be attached, thereby securing the probe. To remove the device, the suture attachment wire is simply retracted until it is completely inside the flexible tubing, thereby releasing the sutures. The device is then removed through the insertion wound by pulling on the flexible tubing.

BRIEF DESCRIPTION OF THE DRAWINGS

FIG. 5 is a front elevational view of a second embodiment of the device with the artery shown in phantom dashed line;

FIG. 6 is a fragmentary sectional elevation taken along line 6—6 in FIG. 5;

FIG. 7 shows a second method of suturing the device of FIG. 5 in place;

FIG. 8 shows a third method of suturing the device of FIG. 5 in place;

FIG. 9 shows a third embodiment of the invention, and

FIG. 10 is a fragmentary top elevational view of a fourth embodiment of the inventive device.

DESCRIPTION OF THE PREFERRED EMBODIMENTS

Figure 1:
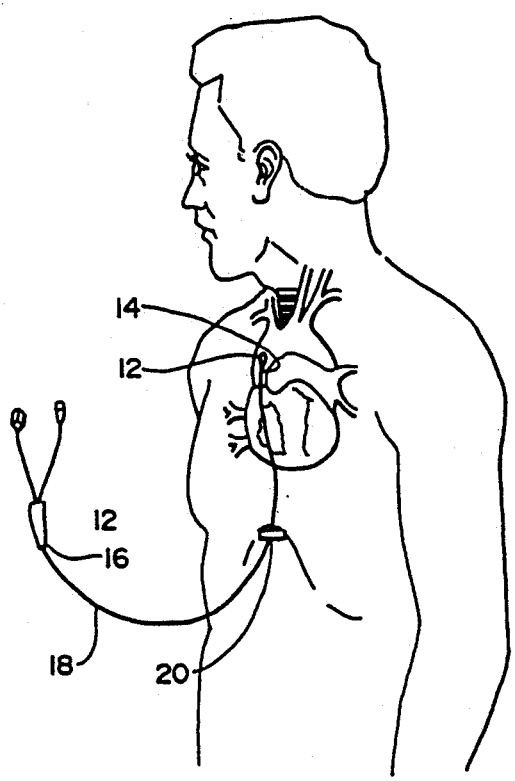
FIG. 1 is a simplified pictorial diagram of the preferred embodiment.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Figure 2:
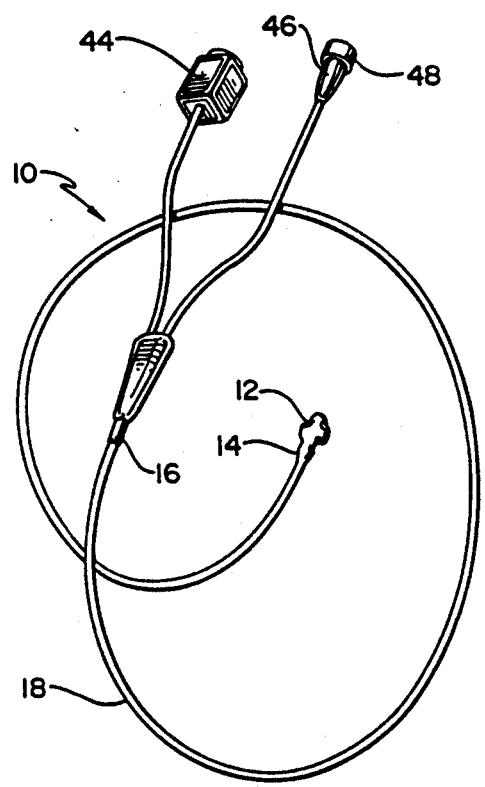
FIG. 2 is a perspective of FIG. 1.

Referring now to FIGS. 1 and 2, the inventive implantable and removable device or probe is shown generally at 10. The device is comprised of a transducer support 12 carried at the distal end 14 of the device, and which is connected to the proximal end 16 of the device by means of a flexible tube 18, as is well known in the art. The device is inserted into the body through insertion wound 20, then implanted on a vessel, such as an artery or vein. The device is primarily intended for use in monitoring blood flow through arteries or veins, but could also be used on other organs. The device is approximately ⅜ inch long and ⅛ inch in cross-section. The device is intended to be secured onto the vessel such that it would lie generally axially along the vessel.

Figure 3:
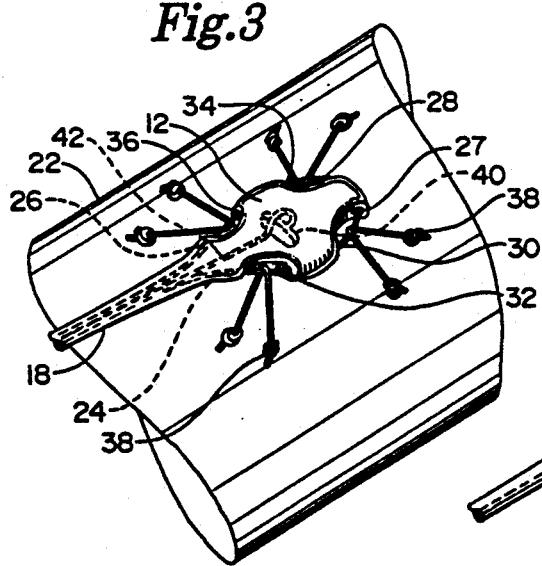
FIG. 3 is a fragmentary perspective view of the device implanted.
Figure 4:
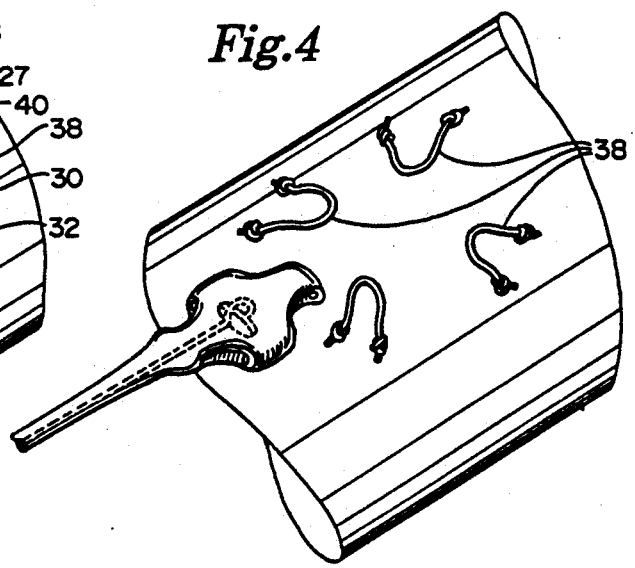
FIG. 4 is a fragmentary perspective view of the device during withdrawal.

Referring now to FIGS. 3 and 4, transducer support 12 is shown secured to artery 22. In the preferred embodiment, a pair of release wires 24 and 26 extend through the flexible tubing 18 and are releasably attached to the front of transducer support 12 by insertion into wire channels 27 and 28. In the preferred embodiment, wires 24 and 26 are held in wire channels 27 and 28 by means of a compression spring (discussed more fully in connection with FIG. 10). However, wires 24 and 26 or wire channels 27 and 28 could be sized so that the wires 24 and 26 were friction or compression loaded into wire channels 27 and 28.

As can be seen best in FIGS. 3 and 4, wires 24 and 26 are exposed at cut-outs 30, 32, 34 and 36, to allow sutures 38 to be attached to transducer support 12 to secure the transducer support 12 to the monitor site. The transducer is comprised of a generally flat piezoelectric crystal 40 which is mounted at an angle of between 5° and 85°, as is well known in the art. The preferred angle is approximately 50°, which provides a good compromise between measuring blood flow and vessel diameter, as is well known in the art. It should also be understood that the angle is measured between a line perpendicular to the vessel and the face of crystal 40. Lead wires 42 extend through flexible tubing 18 and are attached to electrical connector 44 (shown in FIG. 2) for ease of connection to a monitoring device, as is well known in the art.

Release wires 24 and 26 can be extracted from channels 27 and 28 via detach access port 46 (shown in FIG. 2). Cap 48 is removed, wires 24 and 26 are pulled out of channels 27 and 28, thereby releasing transducer support 12 from sutures 38, as shown in FIG. 4. The transducer support 12 can then be withdrawn from the body by pulling on flexible tube 18. The transducer can be extracted through insertion wound 20 without the need for surgery.

Referring now to FIGS. 5 through 8, an alternate embodiment of the inventive device is shown. An elongate probe body 50 (best seen in FIG. 6) is attached at the distal end of a flexible tube (not shown). Probe body 50 contains a wire channel 52 which has an opening 54 which opens to suture access space 56. The front end 58 of probe body 50 contains a wire channel 60 for frictional engagement with the distal end of release wire 62. FIG. 5 shows how a series of sutures 38 can be looped around release wire 62, and secured to the vessel at 66 and 68. FIG. 7 shows an alternate attachment method in which the suture 38 is looped around the release wire 62, with both ends being attached on the same side of the vessel. FIG. 8 shows how a suture could be looped around release wire 62 and then looped around the entire circumference of the vessel. In all cases, once release wire 62 is pulled from channel 60 and withdrawn back into channel 52, all sutures are disconnected from probe body 50, thereby freeing it for withdrawal.

Referring now to FIG. 9, a third embodiment of the invention is shown of releasably securing the probe body (of FIG. 6) or the transducer (of FIG. 1) to the vessel. Reference numeral 70 refers to a balloon which can be inflated with saline solution, air or other suitable solution, via conduit 72. Balloon 70 would be inflated via a pilot cuff and luer fitting (not shown), which are well known in the art, then sutures 38 attached across balloon 70, thereby securing it in place at the monitoring site. To release the probe body, the balloon would be deflated, and the probe body would be withdrawn, leaving the sutures in place.

It was discovered through experimentation that bending the flexible tube 18 caused a ±1 centimeter slack at the distal end 14 of the device. This slack would sometimes result in wires 24 and 26 being prematurely pulled out of wire channels 27 and 28. FIG. 10 shows a fourth embodiment of the invention which is a modification to the release system designed to overcome this problem, discussed with reference to FIGS. 1 through 4, although it could be easily modified to work with the alternate embodiment discussed with reference to FIGS. 5 through 8. In this embodiment release wires 24 and 26 are in fact two ends of a single piece of wire. The wire is bent in half at loop end 80 and fixed to a loop plug 81 which is inside detach access port 46 (shown in FIG. 2). A compression spring, shown schematically at 82 keeps a constant force on plug 81 via cap 48. This constant force aids in keeping the wire ends 24 and 26 firmly inside channels 27 and 28 while flexible tube 18 is being bent back and forth.

It is not necessary that release wires 24 and 26 be two ends of a single wire. Release wires 24 and 26 could be two separate wires connected to plug 81. It would also be possible to invert the embodiment shown in FIG. 10. Wire channels 27 and 28 could be connected and loop end 80 could run through these channels, with the ends 24 and 26 extending back through the flexible tube. To release the device, one end would be pulled until the other end had been pulled through both wire channels and back into the flexible tube 18, thereby releasing the device from any sutures.

It should be understood that the implanted device could carry any biological sensor, not just a doppler transducer for measuring blood flow. It should also be understood that all parts of the invention placed inside the body are made of a biocompatible material such as plastic or rubber, as is well known in the art. It should also be understood that the wire could be made of a flexible metal, plastic, or monofilament. Although in the embodiment described with reference to FIG. 10, the wire must be flexible but rigid so as to transmit the force applied by spring 82.

This completes the description of the preferred and alternate embodiments of the invention. Those skilled in the art may recognize other equivalents to the specific embodiment described herein which equivalents are intended to be encompassed by the claims attached hereto.

What is claimed is:

1. An implantable, extractable probe for attachment to a vessel or organ comprising:

(a) an elongate probe body having front and rear ends, the elongate probe body terminating in a flexible tube;
(b) at least one biological sensor attached to the probe body;
(c) at least one lead wire connected to the biological sensor, said lead wire extending through the flexible tube;
(d) an inflatable balloon situated on the probe body; and
(e) suture securing means attached to the probe body and looped over the balloon, such that the probe body is secured by inflating the balloon and released for extraction from the body by deflating the balloon.

2. The implantable, extractable prove of claim 1 wherein the biological sensor is an ultrasound transducer.

3. The implantable, extractable probe of claim 2 wherein the biological sensor is attached to the probe body so that upon implantation, said sensor will rest at a 5°–85° angle to a predetermined sensor site.

* * * * *

UNITED STATES PATENT AND TRADEMARK OFFICE
CERTIFICATE OF CORRECTION

PATENT NO. : 5,284,146
DATED : February 8, 1994
INVENTOR(S) : Czar et al

It is certified that error appears in the above—identified patent and that said Letters Patent is hereby corrected as shown below:

Col. 6, line 4, delete "prove" and insert -- probe --

Signed and Sealed this

Fifth Day of July, 1994

Attest:

BRUCE LEHMAN

Attesting Officer

Commissioner of Patents and Trademarks